United States Patent [19]
Whipple et al.

[11] Patent Number: 5,702,469
[45] Date of Patent: Dec. 30, 1997

[54] THUMB JOINT PROSTHESIS AND RELATED METHOD OF IMPLANTATION

[75] Inventors: Terry L. Whipple, Richmond, Va.; Glynnis E. Stone, Mill Valley, Calif.

[73] Assignee: Kinetikos Medical, Inc., San Diego, Calif.

[21] Appl. No.: 588,432

[22] Filed: Jan. 18, 1996

[51] Int. Cl.$^6$ .................................................. A61F 2/42
[52] U.S. Cl. .................................................. 623/21; 623/18
[58] Field of Search .................................................. 623/16, 18, 20, 623/21, 22

[56] References Cited

U.S. PATENT DOCUMENTS

| | | | |
|---|---|---|---|
| 2,422,302 | 6/1947 | Horn | 3/12 |
| 3,694,821 | 10/1972 | Moritz | 3/1 |
| 3,889,300 | 6/1975 | Smith | 623/21 |
| 4,059,854 | 11/1977 | Laure | 3/1.91 |
| 4,156,296 | 5/1979 | Johnson et al. | 623/21 |
| 4,276,660 | 7/1981 | Laure | 3/1.91 |
| 4,304,011 | 12/1981 | Whelan, III | 3/1.91 |
| 4,313,232 | 2/1982 | Habal et al. | 3/1.91 |
| 4,352,212 | 10/1982 | Greene et al. | 3/1.91 |
| 4,636,218 | 1/1987 | Fukuura et al. | 623/18 |
| 4,673,408 | 6/1987 | Grobbelaar | 623/20 |
| 4,955,916 | 9/1990 | Carignan et al. | 623/21 |
| 5,549,690 | 8/1996 | Hollister et al. | 623/21 |

OTHER PUBLICATIONS

Johnson & Johnson Products Inc., "The Biomeric™ Finger Prosthesis" (copyright, 1982).
SDSi Medical Products Division, "New Aids to Effective Hand Surgery" *J. Hand Surg.*, p. 8 (Mar., 1978).
DePuy, "A Case for Stability . . . ", J. Hand Surgery, p. 12 (Jul., 1978).

Benoist Girard & Co., "Trapezo–Metacarpal Arthroplasty" of Dr. J.Y. de la Caffiniere (undated).

Lima–Lto, "Tripodal–Digital Titanium ALV64" (undated).

*Primary Examiner*—David Isabella
*Attorney, Agent, or Firm*—Richard E. Jenkins, P.A.

[57] ABSTRACT

A trapezium-metacarpal thumb joint prosthesis having a metacarpal component for insertion into a metacarpal bone of a human thumb and a trapezium component for insertion into a trapezium bone of a human thumb. The metacarpal component has a forward end of generally truncated hemispherical shape with a convex surface and a rear end having a base and a stem. The trapezium component has a forward end of a generally cylindrical shape with a concave surface with a radially built up shoulder and a rear end having a base and a stem. The concave surface is adapted for non-captive rotational abutment with the convex surface. Also, a related method for implantation of the prosthesis into the metacarpal and trapezium bones of a human thumb, wherein the two components are respectively inserted into a pre-cut void in each of the respective bones from a direction above the radial side of the thumb substantially transverse to the longitudinal axis of each respective bone of the thumb.

10 Claims, 3 Drawing Sheets

THUMB JOINT PROSTHESIS AND RELATED METHOD OF IMPLANTATION

TECHNICAL FIELD

The present invention relates to prosthetic devices for surgical implantation in a human body, and is particularly directed to a thumb joint prosthesis in which components may, during the surgical process, be implanted into the trapezium and the metacarpal of the trapezio-metacarpal joint of the thumb.

BACKGROUND OF THE INVENTION

Various prosthetic devices for replacement of many parts of the human body have been developed over the last 35 years. The development of any prosthetic device presents numerous problems, and in particular, prosthetic devices intended for human joints present unique difficulty since joints must be capable of movement, and, preferably, the device should simulate as closely as possible the natural movement and stability of the particular joint.

While most human joints flex in only one plane, a few joints, such as the hip, the shoulder, and the trapezio-metacarpal thumb joint are moveable throughout substantially an entire hemisphere. Clearly, the creation of prostheses for these joints is especially difficult. Despite several prior attempts to provide a trapezio-metacarpal thumb joint prosthesis, none of the prior art devices has been found to be entirely satisfactory. Some of the prior art devices are very complex and thus quite expensive to manufacture. The more successful of the prior art devices have employed a ball-and-socket component to allow for pivotal movement after the device is implanted in a human hand.

For instance, U.S. Pat. No. 4,955,916 to Carignan et al. describes a thumb joint prosthesis having a ball-and-socket. The trapezium component of the prosthesis (referred to in the '916 patent as the carpal component) includes a socket cavity containing an insert formed of ultra-high molecular weight polyethylene. The insert has a recess with curved interior walls, and one end of the intermediate member of the prosthesis includes a spherical ball rotatably and captively mounted within the recess in the polyethylene insert. The other end of the intermediate member is shrunk fit into a tapered recess in the metacarpal component of the prosthesis. The device is implanted along the respective longitudinal axes of the trapezium bone and the metacarpal bone of the thumb.

Additionally, of interest is the thumb joint prosthesis disclosed in U.S. Pat. No. 4,276,660 to Laure. This prosthesis has a metacarpal component adapted for insertion into the first metacarpal bone of the thumb along its longitudinal axis and carrying thereon the ball portion of a ball-and-socket joint. The prosthesis also has a base portion of flexible material defining a socket into which the ball is snapably and thus captively received. The base includes a projection for reception into a suitably prepared recess in the trapezium bone of the thumb along its longitudinal axis.

Of some relevance are the various ball-and-socket artificial joints shown in U.S. Pat. No. 2,422,302 to Horn; U.S. Pat. No. 3,694,821 to Moritz; and U.S. Pat. No. 4,636,218 to Fukuura et al. Also, of some relevance are various finger joint prostheses for generally hinged movement as shown in U.S. Pat. No. 4,059,854 to Laure; U.S. Pat. No. 4,304,011 to Whelan; U.S. Pat. No. 4,313,232 to Habal et al.; and U.S. Pat. No. 4,352,212 to Greene et al.

Thus, previous trapezio-metacarpal thumb joint prostheses all have a concave surface and a convex surface captively contacting each other, by means of a spherical convex piece (i.e., the ball portion) fitting into a greater than hemispherical concave piece (i.e., the socket portion). Since these prostheses are fully captive, the motion of the hand containing such a prosthesis implanted in the hand tends to cause the prosthesis to break down at the implant-bone interface and components of the prosthesis become loose. Moreover, due to the captivation, the device has to be implanted longitudinally along the respective longitudinal axes of the metacarpal bone and the trapezium bone of the thumb, necessitating extreme distraction of the two bones of the joint during the implantation surgery.

Thus, there has been a long-felt need, solved by the present invention, for a relatively easy to implant trapezio-metacarpal thumb joint prosthesis such that the components of the prosthesis are not fully captive with each other, and yet the prothesis will afford motion and stability like that of a natural trapezio-metacarpal thumb joint.

SUMMARY AND OBJECTS OF THE INVENTION

Accordingly, the present invention provides an improved trapezio-metacarpal thumb joint prosthesis adapted for implantation into a metacarpal bone and a trapezium bone of a joint of a human thumb. The prosthesis comprises a trapezium component and a metacarpal component.

The metacarpal component has a forward end and a rear end. The forward end is of a generally truncated hemispherical shape and has a convex surface. The rear end has a base and a stem, and the stem is adapted for insertion into a pre-cut recess in a pre-selected thumb metacarpal bone from a direction above the radial side of the thumb and substantially transverse to the longitudinal axis of the metacarpal bone.

The trapezium component has a forward end and a rear end. The forward end is of a generally cylindrical shape and has a concave surface that is adapted for non-captive rotational abutment with the convex surface of the metacarpal component. The concave surface of the trapezium component has a radially built up shoulder, which obviates subluxation of the trapezio-metacarpal thumb joint after implantation of the prosthesis. The rear end has a base and a stem, and the stem is adapted for insertion into a pre-cut recess in a pre-selected thumb trapezium bone from a direction above the radial side of the thumb and substantially transverse to the longitudinal axis of the trapezium bone.

Additionally, the present invention provides a method for implantation of the trapezio-metacarpal thumb joint prosthesis described above into a trapezium bone and a metacarpal bone of a human thumb. The method comprises providing a pre-selected thumb metacarpal bone and pre-selected thumb trapezium bone, followed by cutting a recess in each of the two bones.

In order to cut the recess in the two bones, the joint is exposed preferably as follows. A skirt of joint capsule is reflected with or without a sliver of bone from the metacarpal or trapezium, in a proximal or distal direction around a portion of the circumference of the joint, without disarticulating or otherwise exposing the joint surface. The joint surfaces are then resected by sawing, cutting, or milling the bone ends from a direction perpendicular to the long axes of the bones and essentially parallel to the joint surfaces.

After the respective recesses are cut in the two bones, the trapezium-metacarpal thumb joint prosthesis is inserted into the two recesses. The insertion is accomplished by inserting the stem of the metacarpal component into the recess in the metacarpal bone from a direction above the radial side of the thumb and substantially transverse to the longitudinal axis of the metacarpal bone, and inserting the stem of the trapezium component into the recess in the trapezium bone from a direction above the radial side of the thumb and substantially transverse to the longitudinal axis of the trapezium bone. Finally, the convex surface of the metacarpal component is placed against the concave surface of the trapezium component.

Furthermore, the present invention provides a method for implantation of a joint prosthesis into respective first and second bones of a joint of a human body part, the human body part having surgical access from at least one side, such as a radial side, and the first and second bones each having a longitudinal axis. The method comprises (a) providing a human body part, (b) exposing the joint, (c) cutting voids in the bones, (d) implanting a joint prosthesis having a first bone component and a second bone component, and (e) placing the two portions against each other in the following manner. The joint of the human body part may be selected from the group consisting of a hip joint, a shoulder joint, a knee joint, an ankle joint, an elbow joint, a wrist joint, a foot digit joint, and a hand digit joint. Suitably, the hand digit joint is selected from the group consisting of a finger joint and a trapezio-metacarpal thumb joint.

Providing a human body part is accomplished by the human body part having a pre-selected first bone and a pre-selected second bone of a joint, the first and second bones each having bone ends and the joint having a capsule and having a circumference and having surfaces. Exposing the joint is accomplished by: (i) reflecting a skirt of the joint capsule, optionally with a sliver of bone from at least one of the first and second bones, in a proximal or distal direction around a portion of the circumference of the joint, free of disarticulation and other exposure of the surfaces of the joint, and (ii) resecting the joint surfaces by at least one of sawing, cutting, and milling the bone ends from a direction perpendicular to the respective longitudinal axes of the first and second bones and essentially parallel to the joint surfaces. For insertion of the prosthesis, a void is made in each of the first and second bones by removal of the respective biological joint surface of each. Alternatively, the voids may be recesses, and an optional recess may be cut in the first bone and an optional recess may be cut in the second bone.

Implanting a joint prosthesis is accomplished (i) by the prosthesis having a first bone component having a portion thereof adapted for insertion into the void in the first bone, and a second bone component having a portion thereof adapted for insertion into the void in the second bone, and (ii) by inserting the portion of the first bone component into the void in the first bone from a direction above the surgical access side of the human body part substantially transverse to the longitudinal axis of the first bone and the portion of the second bone component into the void in the second bone from a direction above the surgical access side of the human body part substantially transverse to the longitudinal axis of the second bone. Placing the two portions against each other is accomplished by placing the portion of the first bone component against the portion of the second bone component.

Therefore, it is an object of the invention to provide an improved joint prosthesis which will, when implanted, closely simulate the movement of a natural joint.

More particularly, it is a further object of the invention to provide an improved trapezio-metacarpal thumb joint prosthesis which will, when implanted, closely simulate the movement of a natural trapezio-metacarpal joint of the thumb.

Moreover, it is another object of the invention to provide a less invasive means of implanting artificial joint surfaces into various joints of the human body.

It is an advantage of the invention that since the first bone component and the second bone component (i.e., the metacarpal component and the trapezium component) are not captively constrained with each other, each component can be implanted, respectively, into the first bone and the second bone of the joint (i.e., the trapezium bone and the metacarpal bone of the thumb), from a direction above the radial side of the joint (i.e., the thumb joint) and substantially transverse to the longitudinal axis of each bone, instead of from a direction longitudinally along the respective longitudinal axes of the two bones (like prior art thumb prostheses are implanted), thereby allowing for minimal distraction of the joint during the implantation surgery and preservation of important ligaments which confer stability to the joint.

It is a further advantage of the present invention that as a result of the components being non-captive, the implanted inventive prosthesis will not break down or loosen as readily as prior art joint prosthesis (i.e., thumb-joint prostheses) at the implant-bone interface.

Some of the objects and advantages of the invention having been stated above, other objects will become evident as the description proceeds, when taken in connection with the accompanying drawings as best described below.

DETAILED DESCRIPTION OF THE INVENTION

Figure 1:
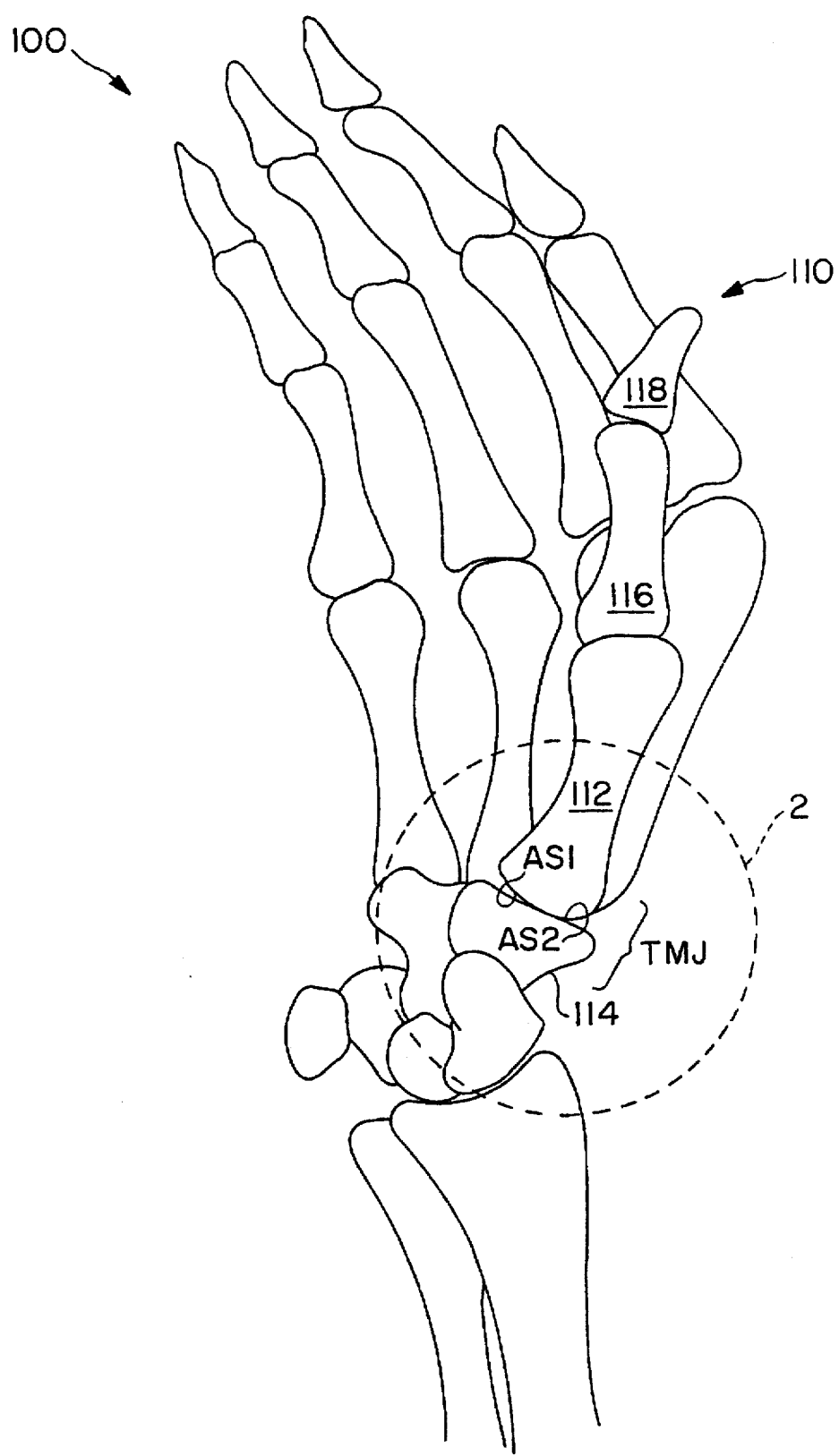
FIG. 1 is a top plan view of the bones of a right human hand.
Figure 2:
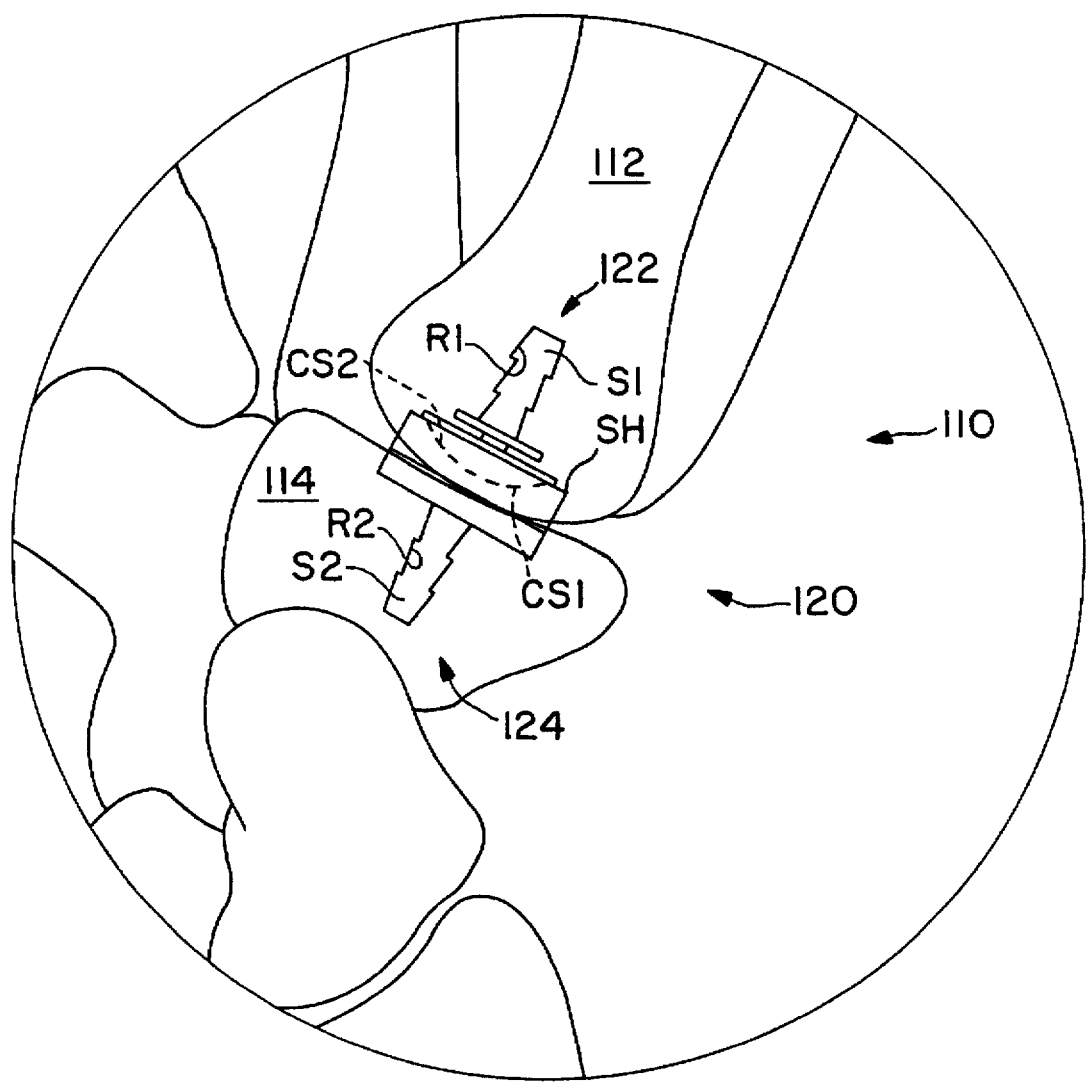
FIG. 2 is an exploded view of the area generally designated by circle 2 in FIG. 1, and further including the trapezio-metacarpal thumb joint prosthesis of the present invention.

Referring now to FIGS. 1–3 of the drawings, like numerals are employed for designating the same components in the various figures.

FIG. 1 shows a diagram from the top surface of the bones of a right human hand, indicated generally as 100. Hand 100 includes thumb 110, comprising metacarpal bone 112 and trapezium bone 114, first phalange 116 and second phalange 118. Metacarpal bone 112 and trapezium bone 114 define trapezio-metacarpal joint TMJ therebetween, with respective articulating surfaces AS1,AS2.

The area of hand 100 generally designated by circle 2 is illustrated in enlarged view in FIG. 2, wherein as shown, the trapezio-metacarpal thumb joint prosthesis of the present invention, indicated generally at 120, is illustrated as implanted at trapezio-metacarpal joint TMJ between metacarpal bone 112 and trapezium bone 114. Trapezio-metacarpal prosthesis 120 includes metacarpal component 122, illustrated as disposed in pre-cut recess R1 in metacarpal bone 112, and also includes trapezium component 124, illustrated as disposed in pre-cut recess R2 in trapezium bone 114.

Figure 3A:
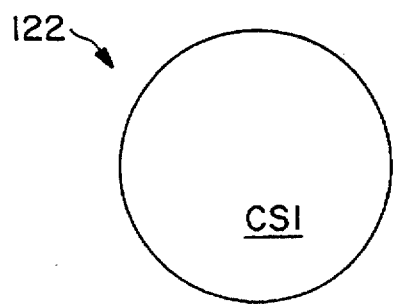
FIGS. 3A–3D are, respectively, a top plan view, a first side view, a second side view rotated 90° from the first side view, and a perspective view of the metacarpal component of the trapezio-metacarpal prosthesis shown in FIG. 2.
Figure 3E:
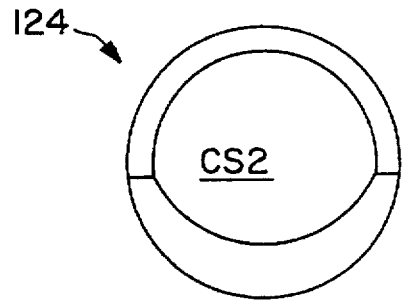
FIGS. 3E–3H are, respectively, a top plan view, a first side view, a second side view rotated 90° from the first side view, and a perspective view of the trapezium component of the trapezio-metacarpal prosthesis shown in FIG. 2.
Figure 3B:
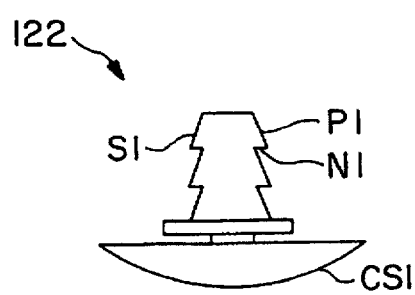
Figure 3F:
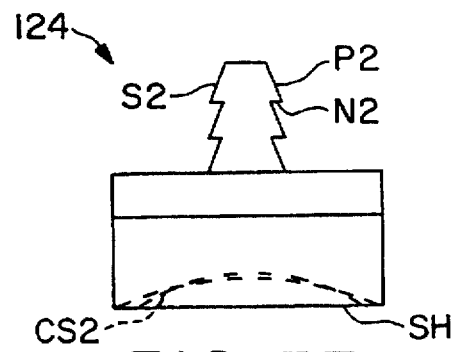
Figure 3C:
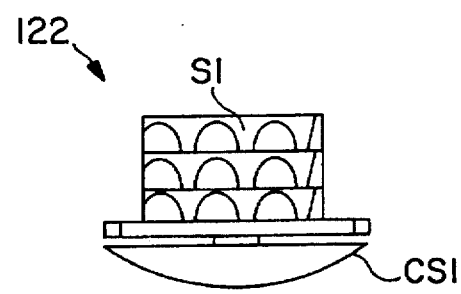
Figure 3G:
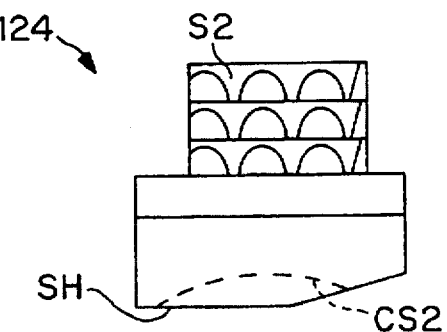
Figure 3D:
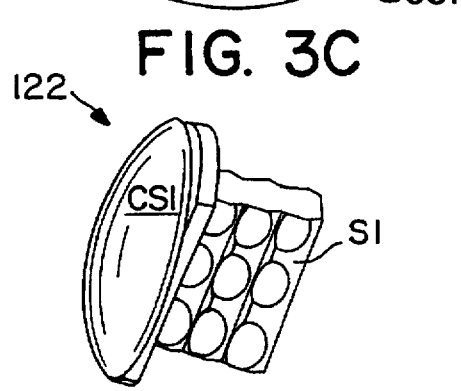
Figure 3H:
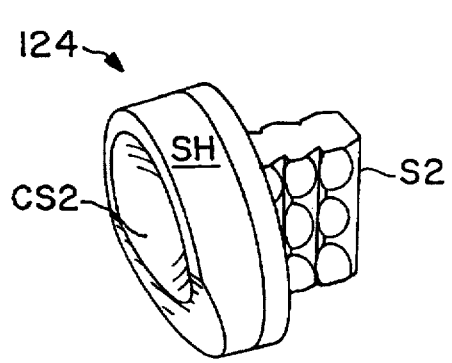

Metacarpal and trapezium components 122,124 can best be seen in FIGS. 3A–3D and in FIGS. 3E–3H, respectively. More particularly, FIG. 3A illustrates a perspective view of metacarpal component 122; FIG. 3B illustrates a side view of metacarpal component 122; FIG. 3C illustrates another side view of metacarpal component 122 rotated 90° on its vertical axis from the side view illustrated in FIG. 3B; and FIG. 3D illustrates a top plan view of metacarpal component 122. Similarly, FIG. 3E illustrates a perspective view of trapezium component 124; FIG. 3F illustrates a side view of trapezium component 124; FIG. 3G illustrates another side view of trapezium component 124 rotated 90° on its vertical axis from the side view illustrated in FIG. 3F; and FIG. 3H illustrates a top plan view of trapezium component 124.

Turning now specifically to FIGS. 3A–3D, metacarpal component 122 includes a forward end of a generally truncated hemispherical shape and having a convex surface CS1, and also includes a rear end having base portion B1 and stem portion S1. Preferably, stem portion S1 may be provided with rough surfaces, for instance, notches N1 and projections P1 (or threads like the threads of a screw, not illustrated), whereby the rough surfaces help keep stem portion S1 in place in metacarpal bone 112.

Turning now specifically to FIGS. 3E–3H, trapezium component 124 includes a forward end portion of a generally cylindrical shape and having a concave surface CS2 with radially built up shoulder SH. As described in more detail below, during implantation surgery, trapezium component 124 is inserted into pre-cut recess R2 such that shoulder SH is oriented toward the radial side of thumb 110 (see FIG. 1), which helps prevent subluxation of trapezio-metacarpal joint TMJ after implantation surgery. Trapezium component 124 also includes a rear end having a base portion B2 and stem portion S2. Preferably, stem portion S2 may be provided with rough surfaces, for instance, notches N2 and projections P2 (or threads like the threads of a screw, not illustrated), whereby the rough surfaces help keep stem portion S2 in place in trapezium bone 114. Concave surface CS2 of trapezium component 124 is adapted for non-captive rotational abutment with convex surface CS1 of metacarpal component 122.

The following is noted with respect to securement means in lieu of providing stems S1,S2 with notches N1,N2 and projections P1,P2 in order to secure trapezio-metacarpal prosthesis 120 to metacarpal and trapezium bones 112,114. As it is well known in the art of implants to secure an implant to a bone with a pin through an aperture in the implant, stems S1,S2 may be provided alternatively with respective apertures (not illustrated) therein so that respective pins (not illustrated) may be inserted therethrough to help keep stems S1,S2 in place in metacarpal and trapezium bones 112,114, respectively, after stems S1,S2 of metacarpal and trapezium components 122,124 have been inserted into respective recesses R1,R2 cut into metacarpal and trapezium bones 112,114 during implantation surgery.

The materials suitable for manufacture of metacarpal and trapezium components 122,124 are as follows. Both stems S1,S2 and bases B1,B2 of rear ends 123,127, respectively, of metacarpal and trapezium components 122,124 may be manufactured of a titanium-aluminum-vanadium alloy, namely $Ti_6Al_4V$. Convex surface CS1 of metacarpal component 122 is suitably manufactured from a cobalt-chromium alloy, namely CoCr, and concave surface CS2 of trapezium component 124 is suitably manufactured from ultra high molecular weight polyethylene. CoCr is hard material that wears well against polyethylene.

METHOD OF USE

In use, during implantation surgery, trapezio-metacarpal joint TMJ is exposed through a short incision just medial to the extensor pollicus longus tendon (not illustrated). The incision in the radial side of thumb 110 is to be parted down over the radial margin of metacarpal bone 112 to the first extensor compartment. Exposure to gain access to the articulating surfaces of trapezio-metacarpal joint TMJ may be achieved by resecting a bone sliver of metacarpal bone 112 with attachment of the extensor pollicus brevis tendon (not illustrated). By resecting the bone/ligament attachment, bone can be sutured back to bone. Bone-to-bone reattachment will heal more quickly and more strongly than a ligament-to-bone attachment and will better preserve the function of the soft tissue.

After the extensor pollicus brevis tendon is detached by removing the bone sliver, the resulting flap or skirt of joint capsule is reflected proximally. Alternatively, the capsule can be reflected in a distal direction by excising a sliver of bone from the distal margin of the trapezium. The capsule is incised longitudinally along the radial edge of the extensor pollicus longus tendon sheath as far proximally as possible, turning the flap of tissue proximally to view trapezio-metacarpal joint TMJ.

The width of trapezio-metacarpal joint TMJ is measured with sizers to determine the desired size for pre-cut recesses R1,R2 as related to the size of respective stems S1,S2. It is desired that pre-cut recesses R1,R2 in metacarpal and trapezium bones 112,114, respectively, be slightly smaller in width than the width of respective stems S1,S2. This feature is especially desirable if stems S1,S2 are going to be provided with roughened surfaces, i.e., notches N1,N2 and projections P1, P2 (instead of respective apertures for respective pins) so that stems S1,S2 may be press-fit into pre-cut recesses R1,R2 in metacarpal and trapezium bones 112,114, respectively, during implantation surgery.

Employing a milling guide with pins for attachment to metacarpal and trapezium bones 112,114, respectively, before the first cuts are made, articulating surfaces AS1,AS2 and the subchondral bones of metacarpal and trapezium bones 112,114 are removed with a mill or a chisel to a depth gauged by etchings on the blade. This forms a step-cut leaving the ulnar-most aspect of trapezium bone 114 intact in order to support trapezium component 124 and to maintain soft tissue attachment. The corners of the milled space are rasped to form a rectangle and the mill guide is removed. Then, as stems S1,S2 are of a generally rectangular parallelepiped shape as can be seen in the preferred embodiment illustrated in FIGS. 2 and 3, a side end mill is employed to cut corresponding rectangular parallelapiped shaped slots for pre-cut recesses R1,R2 for implantation of stems S1,S2.

Next, metacarpal and trapezium components 122,124 are attached with shoulder SH of trapezium component 124 oriented toward the radial side of thumb 110. Stems S1,S2 may be press-fit into recesses R1,R2, and optionally, bone cement (i.e., methyl methacrylate) may be employed to help secure stems S1,S2 to recesses R1,R2. Alternatively, as noted above, if there are no apertures in stems S1,S2, then attachment may be by using pins.

After this, convex surface CS1 of metacarpal component 122 is placed against concave surface CS2 of trapezium component 124, and trapezio-metacarpal joint TMJ is reduced. The area is flushed with copious amounts of antibiotic irrigation solution, followed by reattaching the extensor pollicus brevis ligament and joint capsule to the base of metacarpal bone 112. Then, using sutures, the subcutaneous tissue and skin are closed as separate layers, and a radial gutter plaster splint over sterile dressings is applied. After 10–14 days, the splint and sutures are removed and gentle active motion is allowed.

Furthermore, the present invention, in the broad sense, contemplates a method for implantation of a joint prosthesis into respective first and second bones that define a joint of a human body part. The human body part has a radial side and the first and second bones each has a longitudinal axis. The joint of the human body part may be a hip joint, a shoulder joint, a knee joint, an ankle joint, an elbow joint, a wrist joint, or a hand digit joint, and suitably, the hand digit joint may be a finger joint or a trapezio-metacarpal thumb joint.

The method of implanting the joint prosthesis into the joint of the human body part comprises first providing a human body part having a pre-selected first bone and a pre-selected second bone of a joint, the first and second bones each having bone ends and the joint having a capsule, a circumference, and surfaces. Next, the joint is exposed by: (i) reflecting a skirt of the joint capsule, optionally with a sliver of bone from at least one of the first and second bones, in a proximal or distal direction around a portion of the joint circumference, free of disarticulation and other exposure of the joint surfaces, and (ii) resecting the joint surfaces by at least one of sawing, cutting, and milling the bone ends from a direction perpendicular to the respective longitudinal axes of the first and second bones and essentially parallel to the joint surfaces. After respective recesses are cut in the first and second bones, a joint prosthesis is implanted (i) by the prosthesis having a first bone component having a portion thereof adapted for insertion into the first bone recess, and a second bone component having a portion thereof adapted for insertion into the second bone recess, and (ii) by inserting the portion of the first bone component into the first bone recess from a direction above the radial side of the human body part substantially transverse to the longitudinal axis of the first bone and the portion of the second bone component into the second bone recess from a direction above the radial side of the human body part substantially transverse to the longitudinal axis of the second bone. Then, the portion of the first bone component is placed against the portion of the second bone component so that the two portions against each other.

It will be understood that various details of the invention may be changed without departing from the scope of the invention. Furthermore, the foregoing description is for the purpose of illustration only, and not for the purpose of limitation—the invention being defined by the claims.

What is claimed is:

1. A trapezio-metacarpal thumb joint prosthesis adapted for implantation into a metacarpal bone and a trapezium bone of a trapezio-metacarpal thumb joint a human thumb, the thumb having a radial side and the metacarpal and trapezium bones each having a longitudinal axis, said prosthesis comprising:

(a) a metacarpal component having (i) a forward end of a generally truncated hemispherical shape and having a convex surface, and (ii) a rear end having a stem, and the stem being adapted for insertion into a pre-cut void in a pre-selected thumb metacarpal bone from a direction above the radial side of the thumb substantially transverse to the longitudinal axis of the metacarpal bone; and (b) a trapezium component having (i) a forward end of a generally cylindrical shape and having a generally concave surface, the concave surface being adapted for non-captive rotational abutment with the convex surface of the metacarpal component, and (ii) a rear end having a stem, and the stem being adapted for insertion into a pre-cut void in a pre-selected thumb trapezium bone from a direction above the radial side of the thumb substantially transverse to the longitudinal axis of the trapezium bone.

2. The trapezio-metacarpal thumb joint prosthesis of claim 1, wherein the generally concave surface of the trapezium component includes a radially built up shoulder to prevent subluxation after implantation.

3. The trapezio-metacarpal thumb joint prosthesis of claim 1, wherein the stem of the metacarpal component and the stem of the trapezium component each is of a generally parallelapiped shape.

4. The trapezio-metacarpal thumb joint prosthesis of claim 1, wherein the stem of the metacarpal component and the stem of the trapezium component are each provided with respective notches and projections for securement of the respective metacarpal and trapezium components to the respective metacarpal and trapezium bones of the thumb.

5. A method for implantation of a trapezio-metacarpal thumb joint prosthesis into a trapezium bone and a metacarpal bone of a trapezio-metacarpal thumb joint of a human thumb, the thumb having a radial side and the metacarpal and trapezium bones each having a longitudinal axis, said method comprising:

(a) providing a hand having a pre-selected thumb metacarpal bone and a pre-selected thumb trapezium bone;

(b) cutting a void in the metacarpal bone and a void in the trapezium bone;

(c) implanting a trapezio-metacarpal thumb joint prosthesis comprising:

(I) a metacarpal component having
      (i) a forward end of a generally truncated hemispherical shape and having a convex surface, and
      (ii) a rear end having a stem, and (II) a trapezium component having (i) a forward end of a generally cylindrical shape and having a concave surface, the concave surface being adapted for non-captive rotational abutment with the convex surface of the metacarpal component, and (ii) a rear end having a base and a stem, by inserting the stem of the metacarpal component into the void in the metacarpal bone from a direction above the radial side of the thumb substantially transverse to the longitudinal axis of the metacarpal bone and the stem of the trapezium component into the void in the trapezium bone from a direction above the radial side of the thumb substantially transverse to the longitudinal axis of the trapezium bone; and (d) placing the convex surface of the metacarpal component against the concave surface of the trapezium component.

6. The method of claim 5, wherein, in order to cut the recesses in the metacarpal bone and trapezium bones of the thumb joint, the bones having bone ends and the thumb joint having a capsule and having a circumference and having surfaces, step (b) further comprises exposing the thumb joint by:

(i) reflecting a skirt of the thumb joint capsule, optionally with a sliver of bone from at least one of the metacarpal bone and the trapezium bone, in a proximal or distal direction around a portion of the circumference of the thumb joint, free of disarticulation and other exposure of the surfaces of the thumb joint, and (ii) resecting the thumb joint surfaces by at least one of sawing, cutting, and milling the bone ends from a direction perpendicular to the longitudinal axes of the metacarpal and trapezium bones and essentially parallel to the thumb joint surfaces.

7. The method of claim 5, wherein the generally concave surface of the trapezium component of the thumb joint prosthesis includes a radially built up shoulder to prevent subluxation after implantation.

8. The method of claim 5, wherein the stem of the metacarpal component is of a generally parallelapiped shape and the recess in the metacarpal bone is of a corresponding generally parallelapiped shape and the stem of the trapezium component is of a generally parallelapiped shape and the recess in the trapezium bone is of a corresponding generally parallelapiped shape.

9. The method of claim 8, wherein the voids are recesses and the recess in the metacarpal bone has a width slightly smaller than that of the stem of the metacarpal component and the recess in the trapezium bone has a width slightly smaller than that of the stem of the trapezium component, whereby during insertion, the respective stems are press-fit into the respective recesses.

10. The method of claim 5, wherein the stem of the metacarpal component is provided with an aperture therethrough for insertion of a pin to secure the metacarpal component to the metacarpal bone and the stem of the trapezium component is provided with an aperture therethrough for insertion of a pin to secure the trapezium component to the trapezium bone.

* * * * *